United States Patent
Ericsson et al.

(10) Patent No.: US 6,706,252 B1
(45) Date of Patent: Mar. 16, 2004

(54) METHOD OF TREATING DISEASE WITH RADIOISOTOPES CONJUGATED TO BIOACTIVE SUBSTANCES

(75) Inventors: Arthur Dale Ericsson, Houston, TX (US); Daniel Hrna, Houston, TX (US); Thomas J. Maloney, Friendswood, TX (US)

(73) Assignee: RX/IBR Corporation, Houston, TX (US)

( * ) Notice: Subject to any disclaimer, the term of this patent is extended or adjusted under 35 U.S.C. 154(b) by 609 days.

(21) Appl. No.: 09/183,454

(22) Filed: Oct. 30, 1998

(51) Int. Cl.⁷ ............... A61K 51/00; A61M 36/14
(52) U.S. Cl. ............ 424/1.49; 424/1.11; 424/130.1; 424/1.65
(58) Field of Search ............... 424/1.11, 1.65, 424/1.49, 9.1, 130.1, 134.1, 147.1, 148.1; 514/836; 534/7, 10–16; 530/387.1, 387.2, 388.3, 388.35; 435/235.1

(56) References Cited

U.S. PATENT DOCUMENTS

| | | |
|---|---|---|
| 4,775,638 A | 10/1988 | Haisma |
| 5,529,776 A * | 6/1996 | Osther et al. ............ 424/160.1 |
| 5,725,856 A | 3/1998 | Hudziak et al. |
| 5,759,514 A | 6/1998 | Mattes |
| 5,759,517 A | 6/1998 | Anderson et al. |

OTHER PUBLICATIONS

Li et al., "Labeling Monoclonal Antibodies . . . " Bioconjugate Chem. 1994, 5, 101–103.
Lewis et al., "A Facile, Water–Soluble Method . . . " Bioconjugate Chem. 1994, 5, 565–576.

* cited by examiner

*Primary Examiner*—Dameron L. Jones
(74) *Attorney, Agent, or Firm*—John R. Casperson

(57) ABSTRACT

A composition of matter comprises a pathogen-targeting organic moiety which is conjugated to a radioisotope which has a half-life of less than 100 days. The composition can be synthesized by bringing together a radioisotope having a half life of less than 100 days with a greater than stoichiometric amount of a complexing agent so as to form a first mixture containing a reaction product between the radioisotope and the complexing agent; removing the excess complexing agent from the mixture; and bringing together the first reaction product and an antibody substance so as to form a second mixture containing a reaction product between the first reaction product and the antibody substance. The composition is useful for treating infectious diseases caused by pathogens.

16 Claims, No Drawings

METHOD OF TREATING DISEASE WITH RADIOISOTOPES CONJUGATED TO BIOACTIVE SUBSTANCES

BACKGROUND OF THE INVENTION

This invention relates to the delivery of radioisotopes to a disease-causing pathogen using a pathogen-targeting material conjugated to the radioisotope.

It is known to deliver cytotoxic radioisotopes to the nucleus of a tumor cell using a targeting protein or polypeptide conjugated with a radio-labeled nucleic acid-targeting small molecule. See, for example, U.S. Pat. No. 5,759,514. However, the use of radio-isotopes to seek and destroy disease-causing living pathogens such as bacteria or viruses has not heretofore been suggested.

Some strains of bacteria and viruses are very resistant to conventional drug therapy and are capable of killing or seriously debilitating the patient. Some strains are capable of mutating into a predominantly drug resistant form during the course of drug treatment, resulting in the death or debilitation of the patient. The widespread use of a particular drug treatment furthermore favors the genetic selection of strains which are resistant to that particular course of treatment. The presence of drug resistant strains of bacteria and viruses poses a growing world wide health threat.

A method for treating patients which have been infected with a drug-resistant pathogen would be very desirable.

SUMMARY OF THE INVENTION

In one embodiment of the invention, there is provided a composition of matter comprising a living pathogen-targeting organic moiety which is conjugated to a radioisotope which has a half-life of less than 100 days.

A preferred embodiment of the composition of matter can be synthesized by bringing together a radioisotope having a half life of less than 100 days with a greater than a stoichiometric amount of a complexing agent so as to form a first mixture containing a reaction product between the radioisotope and the complexing agent; removing the excess complexing agent from the mixture; and bringing together the first reaction product and an antibody substance so as to form a second mixture containing a reaction product between the first reaction product and the antibody substance.

The invention also provides a method for treating an infectious disease caused by living pathogens. Antibodies produced in response to the pathogens are obtained and replicated. The replicated antibodies are conjugated with a radioisotope which has a half-life of less than 100 days to produce a therapeutic composition. The therapeutic composition is then administered in a manner to bring the therapeutic composition into contact with the living pathogens.

Another method in accordance with the invention for treating an infectious disease caused by living pathogens is carried out by identifying the pathogens causing the infectious disease, selecting a therapeutic composition comprising an organic moiety which is chemically selective for attachment to the pathogens and which is conjugated to a radioisotope which has a half-life of less than 100 days, and administering the therapeutic composition in a manner so that the therapeutic composition becomes attached to the pathogens.

DETAILED DESCRIPTION OF THE INVENTION

In one embodiment of the invention, there is provided a composition of matter comprising a living pathogen-targeting organic moiety which is conjugated to a radioisotope which has a half-life of less than 100 days.

Recent evidence has shown that radioisotopes which emit alpha, beta, or gamma radiation, and especially those of fairly short half-life and which emit Auger electrons during the decay process may be useful for inducing receptor cell specific cytotoxicity.

When a radioisotope decays by orbital electron capture or internal conversion, inner atomic shell vacancies are created in the residual atom. This highly excited atom attains a stable electronic configuration rapidly in a time scale of about $10^{-15}$ seconds via radioactive and non-radioactive transitions. In general, Auger, Coster-Kronig and super Coster-Kronig processes dominate the atomic vacancy cascades. As a result, numerous electrons are ejected from the atom and most of these Auger electrons have very low kinetic energies (about 20–500 eV) with extremely short ranges (a few nanometers) in water. Even though the energy carried by each of these electrons is only a small fraction of the total energy released in the decay process, their collective energy deposition is extremely high. Hence when the decays occur in the immediate vicinity of the critical biological molecules such as DNA, intracellular transmitters or any of the apoptotic cascade mechanisms, the biological effects to that cell are expected to be devastating.

Usually, radioisotopes used in accordance with the invention will have a half-life in the range of from about 1 to about 10 days. Preferably, the radioisotopes emit Auger electrons. Examples of suitable radioisotopes are Phosphorus 32, Copper 67, Gallium 67, Bromine 77, Yttrium 90, Technetium 99, Indium 111, Iodine 125, Iodine 131, Rhenium 186, Rhenium 188, Platinum 195, Bismuth 213, and Astatine 225. Of these, Copper 67, Yttrium 90, Indium 111, Rhenium 186, and Platinum 195 are preferred because these radioisotopes have distinct cytotoxic properties which may be exploited for therapy by the biologically directed targeting. In particular, antibodies labeled with DOTA derivatives incorporating Yttrium 90 and Indium 111 have shown excellent kinetic stability under physiological conditions. Of these two, Indium 111 is most preferred, because of relatively low toxicity to man as compared to Yttrium 90.

Compounds that are labeled with Auger electron emitters are most effective when the compound is internalized within or attached to the cell in a manner capable of activating apoptosis. Auger electrons provide very high-energy emissions but do so over a very short distance or action, which is less than 1–20 microns. This allows for an Auger emitting radioisotope to bring a high energy destructive force into areas to cause critical DNA strand damage (mitochondrial or nuclear). This, in turn activates the mechanism of apoptosis. Therefore, for a radioisotope-ligand to be a particularly desirable therapeutic agent, the compound must have a high cell to be destroyed-to background tissue ratio, a high therapeutic ratio and pharmacokinetic biodistribution profiles that optimize receptor binding, ligand internalization and cellular retention. The effects, therefore, of Auger electron emitters depend upon their cellular and sub-cellular location, which is governed, in turn, by the chemical form of the molecular agent (bioactive substance) to which the radioisotope has been attached.

Generally speaking, the living pathogen-targeting organic moiety is in the form of an antiviral, antifungal or an antibacterial antibody, although fragments of such antibodies or antibiotics which function to selectively carry the radioisotope into or onto a targeted pathogen are also considered suitable. Viruses, fungi, bacteria, or prions may be selected as targets by appropriate selection of the organic moiety. Usually, the organic moiety has a surface chemistry which associates with a surface chemistry of the targeted pathogen.

More preferably, the organic moiety has a surface chemistry to associate with a unique surface chemistry of the targeted pathogen.

Circulating antibodies normally recognize an antigen in the serum or tissue fluids and, furthermore, there are five identifiable classes: IgG, IgA, IgM, IgD and IgE. In addition to antigen binding, all antibodies exert other specific biological activities. The antigen-binding site is usually one in which there is a Fc fragment and two-antigen binding FAB fragments. X-ray crystallography and electron microscopy has provided the structural and biochemical organization of these moieties. Disulfide bonds predominate in cross-linking many of these domains. The primary function of any antibody is to bind any recognizable antigen. Recently, libraries of human specific antibody variable genes have been constructed for recombinant filamentous phages, which display the antibodies on their surface, and it is possible to select from high affinity antibodies for any chosen cell surface antigens from these libraries.

Phage antibodies that bind to a particular antigen may be separated from non-binding phage antibodies by antigen selection and the bound antibodies are recovered by elution. Repeated rounds of selection can isolate antigen-binding phages that were present at the start of the process at frequencies of less than one in a billion.

One technique of producing a homologous population of antibodies of known antigen specificity, are known as hybridomas that are derived from a single B cells and are called monoclonal antibodies. Another technique for producing antibody molecules is named phage antibody or phage libraries. In this case, gene segments encoding antigen-binding variable or V domains of antibodies are fused to genes encoding the coat protein of a bacteriophage. A collection of recombinant phage, each displaying a different antigen-binding domain on its surface is known as a phage display library. Each phage isolated in this way will produce a monoclonal antigen-binding particle analogous to a monoclonal antibody. Genes encoding the antigen-binding site, which are unique to each phage, can then be recovered from the phage DNA and used to construct genes for a complete antibody molecule by joining them to gene segments that encode the invariant parts of an antibody. When these reconstructed antibody genes are introduced into a suitable host cell line, the transferred cells secrete antibodies with all of the desirable characteristics on monoclonal antibodies that are produced from hybridomas.

The antibody binds stably to its antigen as the antibodies recognize the surface features of the native folded protein antigen and the antibody molecules can thus be used to locate their target molecules accurately in single cells or in tissue sections.

Specific examples of bioactive substances that can be used as vectors for the radioisotopes include:

Biologicals:
A. Antiviral antibodies
  1. gp120 and gp41 for HIV virus,
  2. Anti elf-2 antibodies for vaccinia,
  3. Anti-gE/gl antibodies for herpes simplex 1 virus,
  4. Anti IL-10, or BHRF1 antibodies against the Ebstein-Barr virus,
  5. Anti E3 antibodies for adenovirus group.

B. Antibacterial antibodies
  1. C3b, iC3b, MBL, certain oliosaaccharides, and lectins are identifiable markers on gram positive and gram negative cell surfaces and thus serve as markers for vector antibodies.
C. Antibodies toward a unique family of proteins called STATs that also bind DNA.
D. Antibodies directed toward surface LMP-1 antigens that are found on the Ebstein-Barr infected cells, including the EB related papillomas.
E. Antibiotics: Rimafin, streptomycin, tetracycline, puromycin and cyclohemimide all attach to RNA initiation, transcription mechanism of the rapidly reproducing bacteria but Actinomycin D which binds directly to nuclear and mitochondrial DNA while the penicillins and cephalosporins bind directly to the chemokines of the cell wall of the infecting organism. Radioisotopes that are conjugated to an antibiotic would not only enhance the bactericidal but bacteriostatic properties of the drug and but would also reduce the change of drug resistant bacteria.
F. Nonspecific apoptotic antibodies to: Fas ligand, IVCE/CED-3 family, Bcl-2 family, NfkB, CD40L, CLTA-4, TNFR, APO, and TRAF family activate non-selectively the cell destructive mechanism or apoptosis.

Labeling of biologics with radioisotopes for diagnosis and therapy has usually been accomplished through the use of bifunctional chelating agents, which contain both a reactive functionality for covalent attachment to proteins and with a strong nucleotide binding group capable of forming a chemically stable complex with the radioisotope. In the invention, a living pathogen-targeting organic moiety is preferably covalently linked to a complexing agent which binds the radioisotope. A preferred embodiment of the invention uses a bifunctional complexing agent having a reactive functionality covalently attached to the pathogen-targeting organic moiety and a strong nucleotide binding group forming a chemically stable complex with the radioisotope. The strong nucleotide binding group can be in the form of a chelating agent. Examples of suitable chelating agents which can be employed in the invention include ethylenediaminetetraacetic acid (EDTA), diethylenetriaminopentaacetic acid (DTPA), ethyleneglycol-0,0'-bis(2-aminoethyl)-N,N,N',N'-tetraacetic acid (EGTA), N,N'-bis(hydroxybenzyl) ethylenediamine-N,N'-diacetic acid (HBED), triethylenetetraminehexaacetic acid (TTHA), 1,4,7,10-tetraazacyclododecane-N,N',N'',N'''-tetraacetic acid (DOTA), 1,4,7,10-tetraazacyclotridecane-1,4,7,10-tetraacetic acid (TITRA), 1,4,8,11-tetraazacyclotetradecane-N,N',N'',N'''-tetraacetic acid (TETA), 1,4,8,11-tetraazacyclotetradecane (TETRA) and their substituted derivatives. Of these, diethylenetriaminopentaacetic acid (DTPA) and 1,4,7,10-tetraazacyclododecane-N,N',N'',N'''-tetraacetic acid (DOTA) are preferred, because a method that we have modified and employed extensively for the radioactive labeling of bioactive molecules uses diethylenetriaminopentaacetic acid (DTPA) and DOTA as bifunctional chelates which may be achieved by using anhydride (mixed or cyclic) as acylating agents.

A preferred embodiment of the composition of matter can be synthesized by bringing together a radioisotope having a half life of less than 100 days with a greater than stoichiometric amount of a complexing agent so as to form a first mixture containing a reaction product between the radioisotope and the complexing agent; removing the excess complexing agent from the mixture; and bringing together the first reaction product and an antibody substance so as to form a second mixture containing a reaction product between the first reaction product and the antibody substance. Usually, the antibody substance comprises a protein and generally will comprise an immunoglobulin produced by mammalian cells in response to a living pathogen. The complexing agent has a first functional group which reacts with the radioisotope and a second functional group which reacts with a site on the immunoglobulin. Preferably, the first reaction product is ionically neutral, and the process further comprises flowing the first mixture though an anion exchange column to remove excess complexing agent from the mixture. The first reaction product is preferably brought together with a less than stoichiometric amount of the antibody substance to avoid overlabeling, which could reduce effectiveness or cause side effects.

Conventional labeling processes of protein based molecules with augur emitting gamma radioisotopes involves conjugation of the bi-functional agent to the biologic and then this process is followed up with labeling with a radioisotope. Our alternative method, which is called prelabeling, is one in which the bifunctional chelating agent is first radiolabeled and then conjugated to the biologic.

Radiolabeling of antibodies has conventionally been accomplished by prolonged incubation of the conjugate with a radioisotope solution at room temperature. This may, however, result in significant radiolysis of the protein, such as the antibody structure. Rapid and efficient incorporation of the radioisotope onto the bioactive vector (antibody) is demanded in order to afford a high yield and specific activity of the radiolabeled immunoconjugate.

The prelabeling procedure of the invention is defined in the following scheme and contains three basic steps:
1. Radioactive chelate formation in the absence of an antibody (vector)
2. Chelate purification
3. Antibody (bioactive vector) conjugation With the invention, any combination biologic or bioactive substance (vector) may be conjugated with an Auger emitting radio nucleotide. An exemplary procedure of prelabeling is as follows:

Step 1

A bi-directional chelating agent DOTA-Glys3-L (p-isothiocyanate)-Phe-amide was prepared. Carrier free radioisotope (Yt 90 or In 111) in 0.05 M HCL was dried in a heating block under N2 and 100 uL of mM 1 in 0.2 M ammonium acetate (pH 5.0) was added. This mixture was incubated at 37 degrees C. for 30 minutes and then 25 uL of 50 mM DTPA in 0.1M ammonium acetate, (pH 6.0), was added for 15 minutes at room temperature (to complex any remaining radioisotope). The solution was loaded into anion-exchange resin column and this column was spun for 2 minutes at about 2000 g, and this was followed by elution with four 125 uL aliquots of sterile purified water by centrifugation at about 2000 g each. Most of the radioactive chelates for step 2 are recovered in the first four fractions.

Step 2

All of the eluted fractions are collected and concentrated to about 15 uL with a speed-vac concentrator, a step that may be avoided when higher amounts of radioactivity are used. The radiochemical purity of both Yt-90 and In-111 was determined to be greater than 9% by gel filtration HPLC, cellulose acetate electrophoresis and silica gel TLC. Excess chelating agents, complexes containing divalent nucleotides and DPTA complexes are negatively charged. Thus, the DOTA-peptide complexes with trivalent nucleotides can be filtered quickly through an appropriately designed anion-exchange column in water to separate them from anionic species. Thus the neutral chelate avoids the need for more complex processes, in step 2, such as HPLC with mixed organic/aqueous solvents. Prelabeling deals with the impurity problem by using a large excess of chelating agent and then removing this excess, but it does not eliminate trivalent nucleotide complexes from the product.

Step 3

In the conjugation step, a high concentration of antibody (bioactive vector) is desired. In this process each molecule of the chelate isothiocyanate will frequently encounter biovector amino groups with which to react. The concentrated solution is mixed with 1 mg of chimerical mAb (bioactive vector). The pH is adjusted to 9.5 using aqueous 2.0 M triethylamine. This mixture is incubated at 37 degrees for one hour and was isolated using a centrifuged gel-filtration column. At the chosen conjugation conditions of 1 hour incubation at 37C, pH 9.5 the conjugate yield was over 40%, but for radioactivity yields of 100 mCi or greater radiolysis will become important. While the isothiocyanate group on the bifunctional chelating agent is potentially subject to hydrolysis during the labeling and conjugation steps, controlled experiments have demonstrated a loss of less than 5% of the isothiocyanate.

This procedure has several advantages over conventional radiolabeling of antibodies. In step one, the nucleotide chelate formation is easier to control because there is little or no competition form the nucleotide binding sites on the protein and the chelation conditions are not limited by the need to avoid denaturing the protein based antibody. In step 2, excess chelating agent may be removed before the radioactive chelate is attached to the protein, thus avoiding the production of multiply labeled immunoconjugates, each with unfavorable biological properties. Finally, in step three, the antibody is chemically modified and radiolabeled in one step, thereby minimizing the chemical manipulation of the antibody and reducing losses of the radiolabeled antibody chelate. This prelabeling approach permits the use of a large excess of bifunctional chelating agent to achieve a high chelation yield quickly in step one, but it requires a rapid purification method to remove unlabeled reagent in step two.

Radiolabeling of protein conjugates with radioisotopes is sensitive to pH, buffer and temperature effects. The optimum pH for the labeling (step 3) reaction was different for each protein and may be related to the isoelectric point of the protein. Radioisotope incorporation at high specific activity was accomplished in acetate and Tris buffers, while the presence of citrate inhibited the labeling reaction. Increasing the temperature of the radiolabeling reaction to 37–43 degrees greatly increased the efficiency or radioisotope incorporation and the kinetic stability of the radioconjugates.

The chelates that are used for labeling comprise less than 5% of the total attached chelates on the Ab (bioactive vector). In conventional methods of labeling, the excess chelating groups may affect the biological properties of the antibodies by inducing an immune response and impure radioisotope solutions may require larger amounts of the immunoconjugate. With prelabeling, however, a far smaller number of chelates become attached to the antibody and practically all are radiolabeled while the number of multiply modified antibodies is essentially zeroed. These radiolabeled antibodies are nevertheless fully immunoreactive. The efficiency of incorporating a radioisotope into a bioactive chelate is directly proportional to the pH, for example the incorporation increased form 69% at pH 5.5 to 81% at pH 7. The immunoreactivity of radiolabeled Indium 111 and Yttrium 90 onto antibodies was found to be 98.6%. Covalent attachment of DOTA to amines by acylation with the isobutyl formate mixed anhydrides of the chelating agent has been employed to synthesize a variety of DOTA amines. A simple water soluble chemical procedure for the conjugation of DOTA to proteins, by ester attachment, is enhanced by elevated temperature (37–43 degrees), optimum pH (7–9) and appropriate buffer solutions which result in the rapid labeling of radioimmunoconjugates displaying a high specific activity.

The common factor in the use of one of these Radio-nucleotide 1-DOTA or DPTA (chelators)-biovectors-antibody complexes described above is that it attaches only to the surface of the target cells(s) to be destroyed and the emission of Auger energy (Indium 11 or Yttrium 90) is transmitted in tissue only for short distances (10 nm–15 nm) and duration (2–3 day half-life), this activating one of the apoptotic cell destruction mechanisms. The process of apoptosis and cell lysis is pivotal in the explication of the role of induction of antigen/antibody-conjugated-radioisotope triggered cell death using of new created radiolabeled monoclonal/phage antibodies (mAbs).

There are two treatment methods according to the invention. In the first method, the antibodies produced in response to the living pathogens are obtained and replicated. The replicated antibodies are conjugated with a radioisotope which has a half-life of less than 100 days to produce a therapeutic composition. The therapeutic composition is then administered in a manner to bring the therapeutic composition into contact with the pathogens. The second method is carried out by identifying the living pathogens causing the infectious disease, selecting a therapeutic composition comprising an organic moiety which is chemically selective for attachment to the pathogens and which is conjugated to a radioisotope which has a half-life of less than 100 days, and administering the therapeutic composition in a manner so that the therapeutic composition becomes attached to the pathogens.

The preferred radioisotopes to use are those which emit Auger electrons, and in both methods the organic moiety is generally an antibody substance, usually an immunoglobulin or immunoglobulin fragment. The antibody substance is usually conjugated to the radioisotope with a complexing agent as hereinbefore described. The dose to be administered will vary depending on many factors, but will generally be in the range of 1 to 1000 millicuries and in an amount which is adequate to render at least some of the pathogens nonviable. The compositions are preferably combined with a suitable carrier and administered intravenously.

The invention can be applied to treat disease caused by the Human Immunodeficiency Virus, HIV, the retrovirus that causes AIDS. The virus is a double stranded RNA virus 100–120 nm diameter and as its basic structure it has a gag (core protein-p24 and matrix protein-p17 and p7), pol (polymerase/reverse transcriptase-p66/51, p32 and p11) and env (envelope protein) genes. On the surface of the virus are two glycoproteins called the gp 120 and a trans membrane gp 41. The gp120 is responsible for binding to the surface of uninfected CD4 cells (T lymphocytes) by a GP120-CD4 linkage. In fact, the HIV gp120 glycoprotein binds to CD4 resulting in a conformational change that exposes the V3 loop in gp120 and permits the subsequent interaction with a chemokine receptor CXCR4 on the surface of CD4 T cells or CCR5 surface receptor on macrophages in order to gain entry into these cells. Therefore, these chemokine co-receptors are critically involved in the subsequent gp41-mediated fusion and cell internalization. There is widespread immune dysfunction and the host CD4 cells are killed as the virus replicates using the reverse transcriptase as mechanism to usurp the CD4 cell's own DNA. The spectrum of immune dysfunction is characterized by depletion of the CD4 T cells, decrease responses to antigens, mitogens, alloantigens and anti-CD3 antibody, associated with decreased IL-2 production as well as other changes in cytokine production. Finally there is a loss of specific HIV cytotoxic responses and an increase in unresponsive CD8 T cells, increased beta-2 microblobulin and serum neopterin as well as an increase in autoantibodies and immune complexes. The average half life of the virus and other infected cells in the circulation is less than two days, wherein millions of virions are released from infected cells and similar numbers of new cells are infected daily. Antibodies to core and surface proteins may be detected in the serum of infected patients within 2–6 weeks after the initial infection has occurred. Traditional therapy has been nucleoside analogue reverse transcriptase inhibition and polytherapy with non-nucleoside reverse transcriptase inhibitors and carbocyclic nucleoside analogues. Even with aggressive triple-drug combination anti-retroviral therapy, a decrease in HIV-RNA (viral load) plasma levels may not be sustained, and this indicates viral therapy failure. HMV resistance to anti-retroviral agents is likely to be a significant factor contributing to treatment failure in many individuals. This resistance to drug therapy develops because of the error rate of the HIV reverse transcriptase and the high replicative rate of the HIV which leads invariably to frequent mutations in the HIV genome. Resistance to most anti-retroviral agents has been documented in both in vitro and in vivo. There are mechanisms to test for resistance mutations (genotype analysis) or resistance phenotype for virus from any given HIV infected individual and cross-resistance is known to occur.

The HIV virus envelope glycoproteins are less than ideal immunogens since the gp120-gp41 are associated and are buried in the interior of the functional envelope glycoprotein spike outer core. The non-covalent nature of the association between gp120 and gp41 contributes to the lability of the functional envelope glycoprotein titer. Furthermore, the CD4 binding site is recessed and variable regions, which exhibit glycosylation, flank it. Moreover, variable loops, V2 and V3 mask the chemokine receptor-binding site. However, during the natural HIV infection, disassembled envelope glycoproteins elicit most of their antibodies directed toward these viral envelope components. At that time the interactive regions of gp120 and gp41 are particularly antigenic. However, because the cognate antibodies cannot bind the assembled, functional envelope glycoprotein complex, these natural antibodies do not exhibit an effective neutralizing activity. The efficacy of the humoral immune response in vivo is compromised by at least two factors: the relative resistance of primary virus isolates to neutralization and the temporal pattern with which neutralizing antibodies are generated. HIV viruses that have been passaged in immortalized cells lines are typically more sensitive to neutralization by antibodies than are primary clinical isolates. During natural HIV infections, disassembled envelope glycoproteins elicit most of the antibodies directed to these viral components. Antibodies to these envelope proteins typically can be detected in the sera of HIV infected individuals by 2–3 weeks after infection. Later in the course of the HIV infection, antibodies capable of neutralizing a wide range of HIV isolates appear. Human monoclonal antibodies derived from HIV infected individuals have been identified that recognizes the gp120 proteins from a diverse range of HIV isolates. Another fairly conserved gp120 neutralizing epitope is recognized by the 2G12 antibody and bind the gp120 epitope on the outer domain. This 2G12 antibody may recognize more conserved carbohydrate structures that have been formed as a result of a heavy concentration of N-linked glycosylation in the gp120 outer domain. In vivo, the apparent rarity with which the 2G12 antibodies are elicited attests to the success of the viral strategy of using heavily glycosylated outer domain surface in immune evasion. The use of phage 2G12, gp120 and gp41 antibodies will avoid many of the bioactive vector problems.

By exploiting strategies used by the immune system, phage libraries can produce antibodies with many clinically applicable immunochemical specificities. From such libraries, many different antibodies can be isolated against virtually any antigen. Phage antibodies have a number of advantages over monoclonal antibodies produced from hybridomas. First the amino acid sequences of the antibodies are entirely human. Second, in vivo mechanisms that normally get rid of self-reactive antibodies are avoided, because selection occurs mainly in vitro. This makes it possible to produce human antibodies against human antigens. Third the immunoglobulin V genes are already cloned and this increases the affinity of the antibodies, change their fine specificity, and alters their size or valency. Finally, for this purpose, genetic engineering may be used to fuse the antibodies to cytolytic proteins that enhance the therapeutic effect of the antibodies. The ability to produce these phage antibodies is relatively rapid (a few weeks). Therefore, phage antibodies to gp120 and gp41 could be chelated to a radioisotope with a half-life of 2–3 days such as 100 milliCuries of Indium 111 (half-life of 2 days) should be given intravenously to AIDS patients. The course of the RNA viral load, CD4 and CD8 T lymphocytes as well as other markers heralds both the progression and the regression of disease. This potentially curative IV treatment procedure should be repeated every 4–6 months for 3–4 doses, while the response of therapy is scientifically evaluated.

While certain preferred embodiments of the invention have been described herein, the invention is not to be construed as being so limited, except to the extent that such limitations are found in the claims.

What is claimed is:

1. A composition of matter comprising a living pathogen-targeting organic moiety conjugated to a radioisotope which has a half-life of less than 100 days, wherein the living pathogen-targeting organic moiety is covalently linked to a complexing agent which binds the radioisotope, and the living pathogen-targeting organic moiety is linked to the radioisotope via a bifunctional complexing agent.

2. A composition of matter as in claim 1 wherein the bifunctional complexing agent has a first functionality covalently attached to the living pathogen-targeting organic moiety and a second functionality forming a chemically stable complex with the radioisotope.

3. A composition of matter as in claim 1 wherein the bifunctional linking agent comprises a chelating agent.

4. A composition of matter as in claim 3 wherein the chelating agent is selected from the group consisting of ethylenediaminetetraacetic acid (EDTA), diethylenetriaminopentaacetic acid (DTPA), ethyleneglycol-0,0'-bis(2-aminoethyl)-N,N,N',N'-tetraacetic acid (EGTA), N,N'-bis(hydroxybenzyl)ethylenediamine-N,N'-diacetic acid (HBED), triethylenetetraminehexaacetic acid (TTHA), 1,4,7,10-tetra-azacyclododecane-N,N',N",N'"-tetraacetic acid (DOTA), 1,4,7,10-tetra-azacyclotridecane 1,4,7,10-tetraacetic acid (TITRA), 1,4,8,11-tetraazacyclotetradecane-N,N',N",N'"-tetraacetic acid (TETA), and 1,4,8,11-tetraazacyclotetradecane (TETRA).

5. A composition of matter as in claim 4 wherein the chelating agent is selected from the group consisting of diethylenetriaminopentaacetic acid (DTPA) and 1,4,7,10-tetra-azacyclododecane-N, N',N",N'"-tetraacetic acid (DOTA).

6. A method for synthesizing a therapeutic composition, said method comprising reacting a radioisotope having a half life of less than 100 days with a greater than stoichiometric amount of a complexing agent so as to form a first mixture containing a reaction product between the radioisotope and the complexing agent;

removing the excess complexing agent from the mixture; and bringing together the first reaction product and an antibody substance selected from the group consisting of an antiviral antibody, an antifungal antibody and an antibacterial antibody so as to form a second mixture containing a reaction product between the first reaction product and the antibody substance, wherein the antibody substance comprises a protein.

7. A method for synthesizing a therapeutic composition, said method comprising reacting a radioisotope having a half life of less than 100 days with a greater than stoichiometric amount of a complexing agent so as to form a first mixture containing a reaction product between the radioisotope and the complexing agent;

removing the excess complexing agent from the mixture; and bringing together the first reaction product and an antibody substance so as to form a second mixture containing a reaction product between the first reaction product and the antibody substance, wherein the antibody substance comprises an immunoglobulin produced by mammalian cells in response to a pathogen.

8. A method as in claim 7 wherein the complexing agent is bifunctional, having a first functional group which forms a chemically stable complex with the radioisotope and a second functional group which reacts to form a covalent bond with a site on the immunoglobulin.

9. A method as in claim 5 wherein the first reaction product is ionically neutral, said method further comprising flowing said first mixture though an anion exchange column to remove excess complexing agent from the mixture.

10. A method as in claim 6 wherein the first reaction product is brought together with a less than stoichiometric amount of the antibody substance.

11. A method as in claim 6 wherein the radioisotope is selected from the group consisting of Phosphorus 32, Copper 67, Gallium 67, Bromine 77, Yttrium 90, Technetium 99, Indium 111, Iodine 125, Iodine 131, Rhenium 186, Rhenium 188, Platinum 195, Bismuth 213, and Astatine 225.

12. A method as in claim 6 wherein the complexing agent is selected from the group consisting of ethylenediaminetetraacetic acid (EDTA), diethylenetriaminopentaacetic acid (DTPA), ethyleneglycol-0,0'-bis(2-aminoethyl)-N,N,N',N'-tetraacetic acid (EGTA), N,N'-bis(hydroxybenzyl) ethylenediamine-N,N'-diacetic acid (HBED), triethylenetetraminehexaacetic acid (TTHA), 1,4,7,10-tetra-azacyclododecane-N,N',N",N'"-tetraacetic acid (DOTA), 1,4,7,10-tetraazacyclotridecane- 1,4,7,10-tetraacetic acid (TITRA), 1,4,8,11-tetraazacyclotetradecane-N,N',N'',N'''-tetraacetic acid (TETA), and 1,4,8,11-tetraazacyclotetradecane (TETRA).

13. A method for synthesizing a therapeutic composition, said method comprising reacting a radioisotope having a half life of less than 100 days with a greater than stoichiometric amount of a complexing agent so as to form a first mixture containing a reaction product between the radioisotope and the complexing agent;

removing the excess complexing agent from the mixture; and bringing together the first reaction product and an antibody substance so as to form a second mixture containing a reaction product between the first reaction product and the antibody substance, wherein the antibody substance comprises an antiviral antibody selected from the group consisting of anti-gp120 antibody for HIV virus, anti-gp41 antibody for HIV virus, anti elf-2 antibody for vaccinia, anti-gE/gI antibody for herpes simplex 1 virus, anti IL-10 antibody against Ebstein-Barr virus, anti BHRF1 antibody against Ebstein-Barr virus, and anti E3 antibody for adenovirus.

14. A method for treating an infectious disease caused by living pathogens in a mammal, wherein said mammal produces antibodies in response to said living pathogens, said method comprising obtaining antibodies from said mammal;

replicating said antibodies to produce replicated antibodies, conjugating said replicated antibodies with a radioisotope which emits Auger electrons and has a half-life of less than 100 days to produce a therapeutic composition, and administering said therapeutic composition to said mammal in a manner to bring said therapeutic composition into contact with said living pathogens, wherein the antibodies are conjugated with the radioisotope with a complexing agent.

15. A method as in claim 14 wherein in the range of 1 to 1000 millicuries of the therapeutic composition are administered to the mammal.

16. A method for treating an infectious disease caused by living pathogens in a mammal, wherein said mammal produces antibodies in response to said living pathogens, said method comprising obtaining antibodies from said mammal;

replicating said antibodies to produce replicated antibodies, conjugating said replicated antibodies with a radioisotope which emits Auger electrons and has a half-life of less than 100 days to produce a therapeutic composition, and administering said therapeutic composition to said mammal in a manner to bring said therapeutic composition into contact with said living pathogens, wherein the antibodies are conjugated with the radioisotope with a complexing agent, wherein in the range of 1 to 1000 millicuries of the therapeutic composition are administered to the mammal, and wherein the therapeutic composition combined with a pharmaceutically acceptable carrier and is administered intravenously.

* * * * *